United States Patent [19]

Burns

[11] Patent Number: 4,624,253

[45] Date of Patent: Nov. 25, 1986

[54] LANCET

[75] Inventor: James A. Burns, Elizabeth, N.J.

[73] Assignee: Becton, Dickinson and Company, Franklin Lakes, N.J.

[21] Appl. No.: 692,750

[22] Filed: Jan. 18, 1985

[51] Int. Cl.[4] ............................................. A61B 17/34
[52] U.S. Cl. ................................. 128/314; 128/329 R
[58] Field of Search .................... 128/314, 329 R, 305, 128/315, 329 A, 330

[56] References Cited

U.S. PATENT DOCUMENTS

| 1,135,465 | 4/1915 | Pollock | 128/329 |
|---|---|---|---|
| 3,030,959 | 4/1962 | Grunnert | 128/329 |
| 3,383,239 | 8/1967 | Mausteller | 128/329 R |
| 4,157,978 | 5/1985 | Levin et al. | 128/314 |
| 4,203,446 | 5/1980 | Hofert et al. | 128/329 R |
| 4,375,815 | 3/1983 | Burns | 128/314 |
| 4,416,279 | 11/1983 | Lindner et al. | 128/314 |
| 4,449,529 | 5/1984 | Burns et al. | 128/314 |
| 4,462,405 | 7/1984 | Ehrlich | 128/314 |

FOREIGN PATENT DOCUMENTS 2074453 11/1981 United Kingdom ................ 128/314

Primary Examiner—Gene Mancene
Assistant Examiner—J. Hakomaki
Attorney, Agent, or Firm—Robert P. Grindle

[57] ABSTRACT

A disposable lancet assembly is provided, including a housing serving as a lancet-holder guide, a lancet holder body reciprocable in the housing guide, and a flat-bladed lancet mounted in one end of the lancet holder body. Included in the invention are integral strategically positioned abutments which serve dual functions providing snap-action drive for the lancet, together with steps for lancet movement control. The simple coil spring provides damping of the lancet drive in the puncture direction with automatic withdrawal of the lancet into the housing.

7 Claims, 5 Drawing Figures

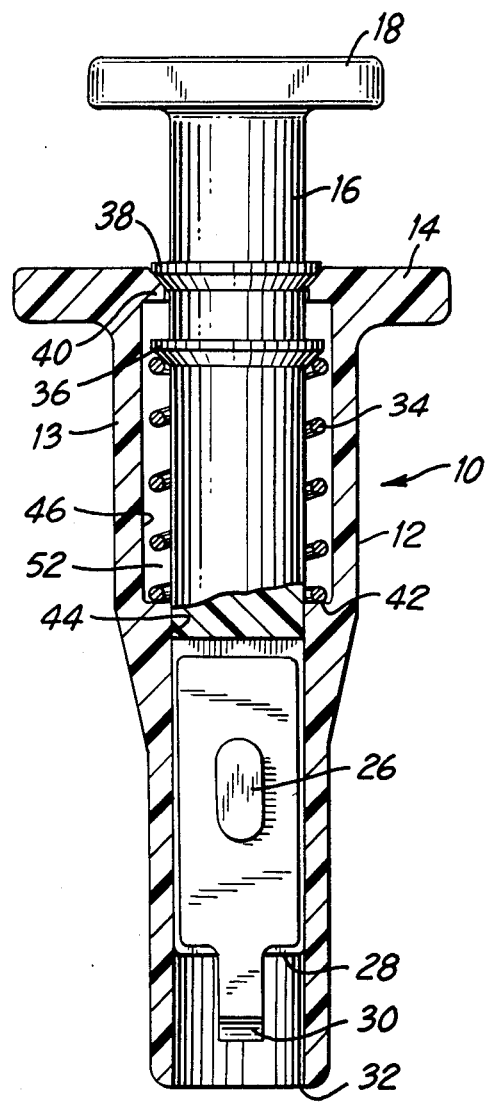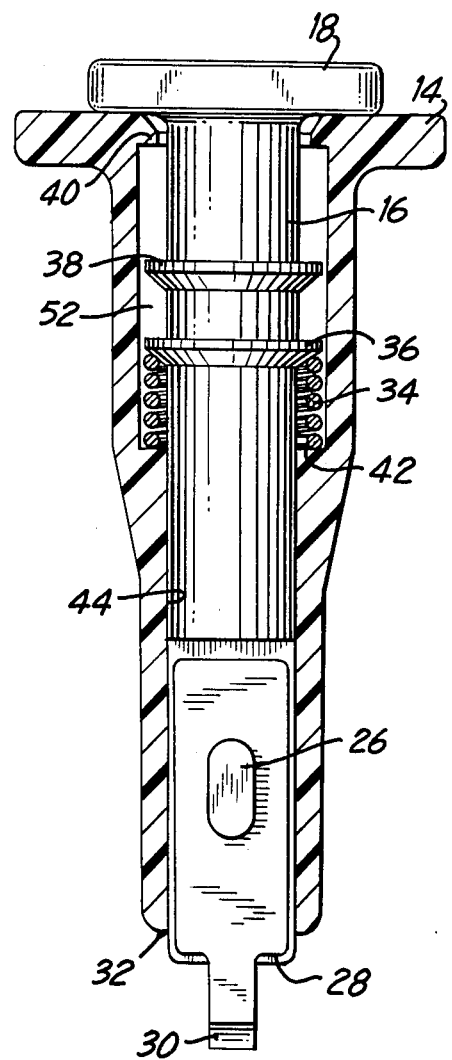
FIG. 1
FIG. 2

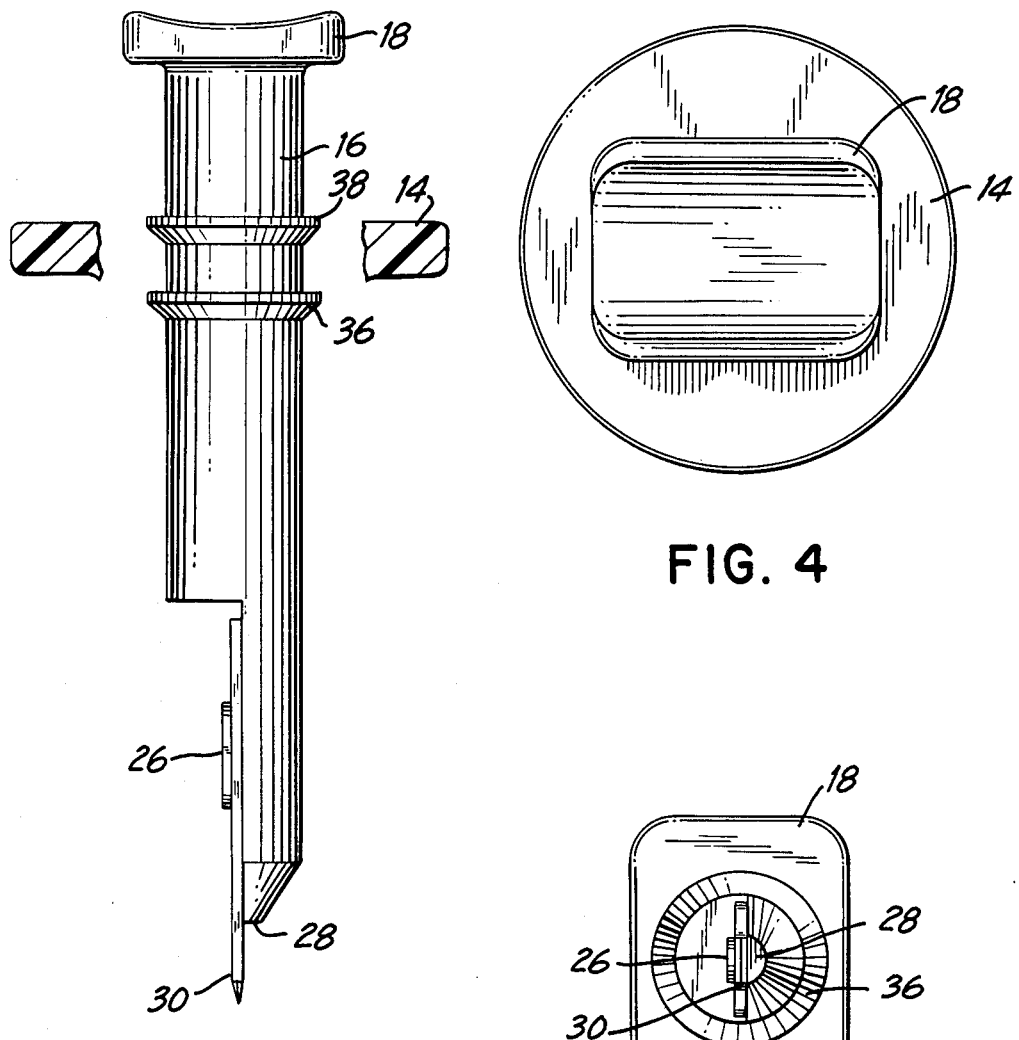

LANCET

BACKGROUND AND DESCRIPTION OF THE INVENTION

This invention relates to the invention described and claimed in co-pending U.S. patent application Ser. No. 652,386, filed Sept. 20, 1984, which is hereby incorporated by reference in its entirety. The present invention relates to a lancet assembly, and more particularly to such an assembly which provides automatic retractable lancet movement, utilizing resilient means incorporated into the assembly having the dual function of damping the lancet drive movement, together with providing the automatic retraction of the lancet once the puncture is made.

Sharp-pointed lancets have been employed for many years to make a quick puncture or penetration of a patient's skin in order to provide a small outflow of blood. Various tests may be employed with only a small amount of blood so that the blood flowing from a finger prick is normally sufficient to carry out a substantial number of tests. However, due to the sensitive nerve endings in the fingertip area, this procedure sometimes induces a significant amount of pain in the patient, even though the skin puncture produces minimal cutting. Moreover, as will be understood, many people are freightened by the appearance of a blade or skin puncture apparatus of any kind wherein the cutting portion is available for them to see prior to the puncture. In order to minimize potential pain, as well as reduce apprehension in a patient, it is desirable to make the thrust of the lancet through the patient's skin rapidly and to provide a rapid withdrawal and shielding of the lancet blade itself.

Other problems involved with such procedures include contamination of the technician in the procedures involved in taking the blood sample. That is, the patient may have some disease, and if the lancet blade which has carried out the puncture action should prick the skin of a technician subsequent to the initial puncture, the technician and/or nurse and/or doctor involved may be exposed to contamination. Thus, it is important to have automatic retraction of the blade immediately after puncture so that the blade is not exposed for an accidental puncture of someone else's skin.

Spring-loaded lancets of different types and forms have been well known and are typified, for example, by U.S. Pat. Nos. 55,620; 1,135,465; 3,030,959; 4,139,011; 4,203,446; 4,230,118; 4,449,529 and 4,88,925.

U.S. Pat. No. 4,203,446, noted above, is significant in that it teaches the puncture of the skin of a patient with a lancet which is retracted back into the device after piercing the patient's skin. In the patented device, the downward motion of the lancet is initiated by impact of a spring-loaded hammer, and as this motion continues the spring potential decreases. At the time of the impact, the return spring begins to compress and increase potential energy. When the potential energy in the return spring under compression exceeds the potential energy in the driving spring, compression of the return spring ends and decompression begins. This, then reverses the motion of the lancet.

However, impact is necessary to compress the return spring and increase its potential energy rapidly. Without the impact force, the spring forces would approach equilibrium and then there would be no reverse motion in order to retract the lancet out of the patient's skin. Moreover, since spring potential is critical in this patented device, a conical spring is relied upon to overcome recoil due to the surge of the larger return spring. Other problems include, of course, the cost of such an involved assembly. Despite the foregoing inventions, improvements in this field of lancets are still being sought.

With this invention, by contrast, an improved automatic retractable throw-away lancet assembly is provided which is relatively simple of construction and easily moldable into two pieces of plastic material. Nevertheless, this simple construction provides, through the utilization of two annular abutments on a lancet holder body assembly cooperating with a single annular integral abutment on a lancet holder guide, a snap action drive for the lancet to rapidly drive the lancet for the puncture action, with an automatic retraction of the lancet once the puncture has been completed. Moreover, a single, conventional coil spring is utilized which first provides a damping of the lancet drive, once the cooperating abutments provide the snap action, and, secondly, provides automatic retraction of the lancet.

In accordance with principles of the present invention, the desired functions are achieved by virtue of a very simplified three-piece structure including a lancet holder guide comprised of a simple elongated piece of semi-rigid material such as a plastic formed into an elongated body having a passage therethrough. Movable in the passage is an elongated lancet holder assembly arranged to have an integral activation handle at one end thereof, and an arrangement for connection of a lancet on the opposite end.

The lancet holder body assembly includes two spaced integral ridges around the perimeter thereof forming abutments. A simple coil spring is mounted between the lancet holder guide and the lancet holder assembly itself. The abutments cooperate with a single integral abutment around the internal perimeter of the lancet holder guide or housing for holding the two parts together prior to use, for providing the snap action in the drive of the lancet to provide the desired puncture, and for providing a stop in both directions of movement of the lancet holder. These two molded pieces together with the spring and the actual lancet blade provide an appropriate and accurate skin puncture for obtaining the desired quantity of blood for carrying out appropriate tests. Moreover, the arrangement is such that it may be immediately discarded without any danger of contamination by subsequent puncture of those who may handle the used lancet assembly. Nevertheless, even though the structure provides the several desired functions of a modern lancet in use, it is easily manufactured by conventional molding procedures.

Other objects and advantages of this invention will be apparent from the following description, the accompanying drawings and the appended claims.

DESCRIPTION OF THE DRAWINGS

FIG. 1 is a longitudinal sectional view of the lancet assembly of the invention in a "prior to use" position;

FIG. 2 is a view of the lancet assembly of FIG. 1 in the position at the moment of puncture;

FIG. 3 is a partial longitudinal side view of lancet holder of the assembly of FIG. 1;

FIG. 4 is a top plan view of the assembly of FIG. 1; and

FIG. 5 is a bottom plan view of the lancet holder of FIG. 3.

DETAILED DESCRIPTION OF THE INVENTION

Referring to the drawings in which like reference characters refer to like parts throughout the several views thereof, FIG. 1 shows a longitudinal sectional view of the lancet assembly 10 of the invention, and includes lancet holder guide housing 12 and lancet holder body assembly 16 reciprocable therein. Lancet holder guide housing 12 includes an elongated lower portion 13 and a wider handle portion 14. Top 18 of lancet holder body 16 serves as the "push-button" for activating the puncture drive motion of the assembly.

FIG. 2 is a view of the assembly of FIG. 1 at the end of the puncture movement.

Referring now to FIG. 3, a partial sectional side view of lancet or blade holder 16 is shown. As can be seen in FIG. 3, the elongated lancet holder body assembly 16 includes lancet holder 26 positioned at the opposite end thereof from the integral push-button top 18. Lancet holder 26 holds lancet blade 30 therein. As can be seen from a comparison of FIGS. 1 and 3, blade 30 is a flat wedge-shaped blade for providing a comparatively elongated puncture wound. Lancet holder 26 includes a flat end edge 28 (FIG. 1), which extends beyond the end 32 of housing 12, (as shown in FIG. 2) in order to engage the skin surface and flatten it during the puncture motion.

Lancet holder body 16 includes, as will be seen in FIGS. 1 and 2, spaced integral abutments 36, 38 or ridges around the perimeter thereof. Abutment 36 cooperates with an internally extending integral abutment 40 on housing 12 at the upper end thereof. Abutment 40 defines the upper end of passage 44 in housing 12 through which lancet holder body 16 reciprocates. Included in passage 44 is a wider portion 46 defining an area 52 in which abutments 36, 38 reciprocate. Area 52 defines the area of movement of coil spring 34 as well. Coil spring 34 extends from abutment 36 to ledge 42 defined by the narrow 44 and wide 46 portions of the passage through which blade holder assembly 16 reciprocates.

Thus, in the initial assembly of the lancet of the invention, lancet holder body housing 16 is pushed into the elongated passage 44 in housing 12. In doing so, abutment 36 is pressed past abutment 40. With this arrangement, housing 16 is prevented from slipping out of housing 12 because abutment 36 engages abutment or stop 40, and prevents such disassembly. Thus, in the position shown in FIG. 1, the lancet assembly of the invention is in a position prior to the puncture movement. In this position, the lower end of blade 30 is positioned inside opening 32 of housing 12. Also in this position, annular abutment 38 is positioned above (as shown in FIG. 1) cooperating abutment 40.

Thus, the user places end 32 of housing 12 in position on the area to be punctured by the lancet. Thereafter, the user pushes the push-button top 18 and forces abutment 38 past abutment 40. This causes a snap action thrust forward which in turn causes blade 32 to engage and puncture the skin surface. During the course of this movement, coil spring 34 is compressed between abutment 36 and ledge 42, as shown in FIG. 2. The effort taken in compressing spring 34 dampens the forward thrust, once the snap action takes place. For this reason, there is no harsh impact of the lower end 28 of lancet holder 26 during the puncture movement. This damping, therefore, minimizes the effect upon a patient during the entire procedure.

During forward movement, top 18 engages handle 14 which limits the extent of forward movement of body assembly 16, and which in turn defines and controls the depth of puncture. In FIG. 3, in an end view of assembly 16, the flat configuration of blade 30 is clearly shown, mounted on holder 26. After skin puncture, coil spring 34 reacts from its compressed position as shown in FIG. 2 and moves to a relaxed state, to a position substantially as shown in FIG. 1. However, abutment 38 engages the bottom of abutment 40.

In the return direction of movement of body assembly 16 in passage 46, abutment 40 serves as a stop for abutment 38. The relaxing of spring 34 and the return to the position with abutment 38 engaging the bottom surface of abutment 40 also causes, automatically, the retraction of blade 30 through opening 32 to a nonexposed position.

FIG. 4 shows a top plan view of the device of FIGS. 1 and 2, and the configuration of push button 18 and the cooperating figure grips or handle 14 on housing 12. FIG. 5 shows a bottom plan view of lancet holder assembly 16, flat blade 30 and lancet holder 26. As can be seen in FIGS. 4 and 5, the flat side of blade 30 is oriented with and in alignment with the rectangular orientation of top or push-button 18. That is, the plane of the long side of push-button 18 is parallel to the plane in which blade 30 is positioned. This allows the user to place the device so that the blade is properly oriented during the puncture movement.

Thus, as will be appreciated from the above, there is provided in accordance with this invention, a retractable throw away lancet assembly which is relatively inexpensive and uncomplicated in its construction, but which, nevertheless, provides a structure for imparting a precise drive and puncture with a precise withdrawal of the lancet in one rapid operation of the assembly. The assembly is comprised of two moldable parts which can be mass produced, as will be understood, from a variety of materials including, for example, polyethylene and polypropylene. Materials should be selected which will provide a degree of resiliency for the purpose of providing cooperative movement relative to the cooperating abutments of the assembly.

While the forms of apparatus herein described constitute preferred embodiments of the invention, it is to be understood that the invention is not limited to these precise forms of apparatus, and that changes may be made therein without departing from the scope of the invention which is defined in the appended claims. For example, whereas one form of spring arrangement is shown for the multi-purpose resiliency required in the arrangement herein, it should be understood that other configurations of integral spring or resilient force may be utilized. Moreover, as stated above, the assembly may be arranged to have a different configuration in cross section. The assembly may be, for example, square or rectangular.

What is claimed is:

1. A lancet assembly comprising,
   (a) an elongated housing;
   (b) a passage extending through said housing with a lancet opening at one end thereof;
   (c) an elongated lancet body reciprocable in said passage;

(d) a lancet blade positioned in said lancet body at one end thereof;
(e) actuation means on said lancet body at the end thereof opposite said lancet blade;
the improvement characterized by
(f) a plurality of spaced apart first integral abutment means on said housing and extending into said passage;
(g) a plurality of spaced apart second integral abutment means on said lancet body for cooperating with said first abutment means;
(h) resilient means extending between said lancet body and said housing;
(i) whereby pushing said actuation means causes said lancet body to move through said passage in a first direction causing one of said second abutment means to move past one of said first abutment means causing a snap-action in a puncture direction and in turn causing said lancet blade to move through said lance opening;
(j) said first movement compressing said resilient means and damping said snap-action;
(k) said first movement stopped by cooperation of said actuation means with said housing; and
(l) release of said actuation means causing relaxation of said resilient means and movement of said lancet body in said passage in a non-puncture direction until engagement of one of said second abutment means with one of said first abutment means for maintaining said lance blade within said housing in a non-contaminating position.

2. The lancet assembly of claim 1, further characterized by
(a) said plurality of first spaced apart abutment means comprising
   (1) an abutment extending into said passage around the perimeter thereof and at the end of said passage opposite said lancet opening; and
   (2) a ledge formed by the intersection of said passage with an enlarged portion thereof, said ledge extending around the perimeter of said passage; and
(b) said plurality of second spaced abutments integral with said elongated lancet body and extending around the perimeter thereof.

3. The lancet assembly of claim 1, further characterized by
(a) said resilient means being a coil spring extending around said lancet body between one of said first abutment means and one of said second abutment means.

4. The lancet assembly of claim 1, further characterized by
(a) a lancet blade holder integral with said lancet body on the end of said lancet body opposite said actuation means; and
(b) said lancet blade holder for mounting said lancet blade.

5. The lancet assembly of claim 1, further characterized by said housing and said lancet body being circular in cross section.

6. The lancet assembly of claim 1, further characterized by
(a) said housing and said lancet body comprised of a resilient plastic material.

7. The lancet assembly of claim 1, further characterized by
(a) said lancet blade is a flat wedge-shaped blade;
(b) said actuation means is a rectangular shaped push-button; and
(c) the long side of said push-button is positioned in a plane parallel to the plane in which said wedge-shaped blade is positioned.

* * * * *